United States Patent
Conlan et al.

(10) Patent No.: US 7,077,942 B1
(45) Date of Patent: Jul. 18, 2006

(54) REMOVAL OF BIOLOGICAL CONTAMINANTS

(75) Inventors: Brendon Conlan, North Ryde (AU); Tracey Ann Edgell, Dee Why (AU); May Lazar, Brighton Le-Sands (AU); Chenicheri Hariharan Nair, Castle Hill (AU); Elizabeth Jean Seabrook, Lane Cove (AU); Thomas Norman Turton, Neutral Bay (AU)

(73) Assignee: Gradipore Limited, Frenchs Forest (AU)

( * ) Notice: Subject to any disclaimer, the term of this patent is extended or adjusted under 35 U.S.C. 154(b) by 291 days.

(21) Appl. No.: 09/887,208

(22) Filed: Jun. 22, 2001

Related U.S. Application Data

(63) Continuation of application No. 09/470,823, filed on Dec. 23, 1999, now Pat. No. 6,464,851.

(30) Foreign Application Priority Data

Dec. 23, 1999 (AU) .............................................. PP7906

(51) Int. Cl.
*B01D 61/42* (2006.01)

(52) U.S. Cl. ....................... 204/543; 204/548; 204/627; 204/644

(58) Field of Classification Search ................. 204/543, 204/548, 627, 644
See application file for complete search history.

(56) References Cited

U.S. PATENT DOCUMENTS

| | | | |
|---|---|---|---|
| 3,878,564 A | 4/1975 | Yao et al. | |
| 4,036,748 A | 7/1977 | Knickel et al. | |
| 4,045,337 A | 8/1977 | Knickel et al. | |

(Continued)

FOREIGN PATENT DOCUMENTS

| | | | |
|---|---|---|---|
| DE | 41 16 179 A1 | | 11/1992 |
| EP | 0 639 945 A2 | | 11/1989 |
| EP | 0 477 541 B1 | | 8/1991 |
| GB | 2 118 975 A | | 2/1983 |
| WO | 93/06475 | | 4/1993 |
| WO | WO 94/22904 | * | 10/1994 |
| WO | WO 97/14486 | | 4/1997 |
| WO | WO 98/21384 | | 5/1998 |
| WO | WO 98/43718 | | 10/1998 |

OTHER PUBLICATIONS

Mullon et al., Forced–Flow Electrophoresis of Proteins and Viruses (1987) Biotechnology and Bioengineering. Vol. XXX pp. 123–137.*

(Continued)

*Primary Examiner*—Arun S. Phasge
(74) *Attorney, Agent, or Firm*—Morgan, Lewis & Bockius LLP

(57) ABSTRACT

A method of removing a biological contaminant from a mixture containing a biomolecule and the biological contaminant, the method comprising: (a) placing the biomolecule and contaminant mixture in a first solvent stream, the first solvent stream being separated from a second solvent stream by an electrophoretic membrane; (b) selecting a buffer for the first solvent stream having a required pH; (c) applying an electric potential between the two solvent streams causing movement of the biomolecule through the membrane into the second solvent stream while the biological contaminant is substantially retained in the first sample stream, or if entering the membrane, being substantially prevented from entering the second solvent stream; (d) optionally, periodically stopping and reversing the electric potential to cause movement of any biological contaminants having entered the membrane to move back into the first solvent stream, wherein substantially not causing any biomolecules that have entered the second solvent stream to re-enter first solvent stream; and (e) maintaining step (c), and optional step (d) if used, until the second solvent stream contains the desired purity of biomolecule.

35 Claims, 3 Drawing Sheets

U.S. PATENT DOCUMENTS

| | | | |
|---|---|---|---|
| 4,045,455 A | 8/1977 | Vogel | |
| 4,069,215 A | 1/1978 | Elfert et al. | |
| 4,115,225 A | 9/1978 | Parsi | |
| 4,123,342 A | 10/1978 | Ahlgren | |
| 4,174,439 A | 11/1979 | Rauenbusch et al. | |
| 4,196,304 A | 4/1980 | Naumann | |
| 4,204,929 A | 5/1980 | Bier | |
| 4,217,227 A | 8/1980 | Elfert et al. | |
| 4,238,306 A | 12/1980 | Perry et al. | |
| 4,238,307 A | 12/1980 | Perry et al. | |
| 4,252,652 A | 2/1981 | Elfert et al. | |
| 4,259,079 A | 3/1981 | Blum | |
| 4,269,967 A | 5/1981 | Elfert et al. | |
| 4,276,140 A | 6/1981 | Jain | |
| 4,279,724 A | 7/1981 | Hearn et al. | |
| 4,299,677 A | 11/1981 | Venkatasubramanian et al. | |
| 4,322,275 A | 3/1982 | Jain | |
| 4,362,612 A | 12/1982 | Bier | |
| 4,376,023 A | 3/1983 | Venkatsubramanian et al. | |
| 4,381,232 A | 4/1983 | Brown | |
| 4,383,923 A | 5/1983 | Elfert | |
| 4,396,477 A | 8/1983 | Jain | |
| 4,441,978 A | 4/1984 | Jain | |
| 4,533,447 A | 8/1985 | Meldon | |
| 4,608,140 A | 8/1986 | Goldstein | |
| 4,661,224 A | 4/1987 | Goldstein et al. | |
| 4,673,483 A | 6/1987 | Mandle | |
| 4,711,722 A | 12/1987 | Toyoshi et al. | |
| 4,746,647 A | 5/1988 | Svenson | |
| 4,749,458 A | 6/1988 | Muroi et al. | |
| 4,780,411 A | 10/1988 | Piejko et al. | |
| 4,897,169 A | 1/1990 | Bier et al. | |
| 4,963,236 A | 10/1990 | Rodkey et al. | |
| 5,039,386 A | 8/1991 | Margolis | |
| 5,043,048 A | 8/1991 | Muralidhara | |
| 5,080,770 A | 1/1992 | Culkin | |
| 5,082,548 A | 1/1992 | Faupel et al. | |
| 5,087,338 A | 2/1992 | Perry et al. | |
| 5,096,547 A | 3/1992 | Klotz et al. | |
| 5,114,555 A | 5/1992 | Stimpson | |
| 5,127,999 A | 7/1992 | Klotz et al. | |
| 5,160,594 A | 11/1992 | Huff et al. | |
| 5,173,164 A | 12/1992 | Egen et al. | |
| 5,185,086 A | 2/1993 | Kaali et al. | |
| 5,238,570 A | 8/1993 | Hugl et al. | |
| 5,277,774 A | 1/1994 | Shmidt et al. | |
| 5,336,387 A * | 8/1994 | Egen et al. | 204/627 |
| 5,340,449 A | 8/1994 | Shukla | |
| 5,352,343 A | 10/1994 | Bailes et al. | |
| 5,407,553 A | 4/1995 | Herron et al. | |
| 5,420,047 A | 5/1995 | Brandt et al. | |
| 5,437,774 A * | 8/1995 | Laustsen | 204/518 |
| 5,441,646 A | 8/1995 | Heller et al. | |
| 5,490,939 A | 2/1996 | Gerigk et al. | |
| 5,503,744 A | 4/1996 | Ikematsu et al. | |
| 5,504,239 A | 4/1996 | Mehl et al. | |
| 5,558,753 A | 9/1996 | Gallagher et al. | |
| 5,561,115 A | 10/1996 | Tenold | |
| 5,565,102 A | 10/1996 | Brandt et al. | |
| 5,610,285 A | 3/1997 | Lebing et al. | |
| 5,650,055 A * | 7/1997 | Margolis | 204/518 |
| 5,662,813 A | 9/1997 | Sammons et al. | |
| 5,723,031 A | 3/1998 | Durr et al. | |
| 5,727,664 A | 3/1998 | Chico | |
| 5,733,442 A | 3/1998 | Shukla | |
| 5,736,023 A | 4/1998 | Gallagher et al. | |
| 5,868,938 A | 2/1999 | Bomer, deceased et al. | |
| 5,891,736 A | 4/1999 | Chapoteau et al. | |
| 5,906,724 A | 5/1999 | Sammons et al. | |
| 5,938,904 A | 8/1999 | Bader et al. | |
| 5,986,075 A | 11/1999 | DuBose et al. | |
| 6,093,296 A | 7/2000 | Soane et al. | |
| 6,117,297 A | 9/2000 | Goldstein | |
| 6,129,842 A | 10/2000 | Kostanian | |
| 6,171,825 B1 | 1/2001 | Chan et al. | |
| 6,464,851 B1 * | 10/2002 | Conlan et al. | 204/543 |

OTHER PUBLICATIONS

Corthals, G.L. et al., Electrophoresis, 1997, vol. 18, No. 3–4, pp. 317–323, "Prefractionation of Protein Samples Prior to Two–Dimensional Electrophoresis" no month.

Horvath, S.J. et al., Electrophoresis, 1996, vol. 17, No. 1, pp. 224–226, "Preparative Affinity Membrane Electrophoresis" no month.

International Search Report Dated May 2, 2000 no month.

Corthals, G.L. et al., Electrophoresis, 1997, vol. 17, No. 4, pp. 771–775, "The Role of pH and Membrane Porosity in Preparative Electrophoresis" no month.

Horvath, S.J. et al., Electrophoresis, 1995, vol. 16, No. 1, pp. 98–100, "Preparative Reflux Electrophoresis" no month.

Horvath, S.J. et al., Electrophoresis, 1994, vol. 15, No. 7, pp. 968–971, "Multifunctional Apparatus for Electrokinetic Processing of Proteins" no month.

Applied and Theoretical Electrophoresis, vol. 3, No. 1, 1992, pp. 13–16, C.W. Wrigley et al, "Rapid (Ten Minute) Pore–Gradient Electrophoresis of Proteins and Peptides in Micrograd Gels" no month.

Journal of Chromatography, vol. 773, No. 1–2, 1997, pp. 229–309, G.L. Corthals et al, "Purification by Reflex Electrophoresis of Whey Proteins and of a Recombinant Protein Expressed in Dictyostelium Discoideum" no month.

Separation Science and Technology, vol. 27, No. 1, 1992, pp. 11–27, J.L. Schmidt et al., "Electrophoresis Along a Semipermeable Membrane Surface" no month.

Journal of Chromatography, vol. 707, No. 1, 1995, pp. 77–85, K.D. Cole et al., "Free–Solution Electrophoresis of Proteins in an Improved Density Gradient Column and by Capillary Electrophoresis" no month.

Biotechnology and Bioengineering, vol. 30, No. 1, 1987, pp. 123–137, C. Mullon et al., "Forced–Flow Electrophoresis of Proteins and Viruses" no month.

* cited by examiner

REMOVAL OF BIOLOGICAL CONTAMINANTS

TECHNICAL FIELD

The present invention relates to methods for the removal of biological contaminants, particularly removal of biological contaminants from biological preparations.

BACKGROUND ART

The modern biotechnology industry is faced with a number of problems especially concerning the processing of complex biological solutions which ordinarily include proteins, nucleic acid molecules and complex sugars and which are contaminated with unwanted biological materials. Contaminants include microorganisms such as bacteria and viruses or biomolecules derived from microorganisms or the processing procedure. The demand is, therefore, for a high purity, scalable separation, which can be confidently used both in product development and production, which in one step will both purify macromolecules and separate these biological contaminants.

Viruses are some of the smallest non-cellular organisms known. These simple parasites are composed of nucleic acid and a protein coat. Viruses are typically very small and range in size from $1.5\times10^{-8}$ m to $5.0\times10^{-5}$ m. Viruses depend on the host cells that they infect to reproduce by inserting their genetic material into the host. Often literally taking over the host's function. An infected cell produces more viral protein and genetic material, often instead of its usual products. Some viruses may remain dormant inside host cells. However, when a dormant virus is stimulated, it can enter the lytic phase where new viruses are formed. Self-assemble occurs and burst out of the host cell results in killing the cell and releasing new viruses to infect other cells. Viruses cause a number of diseases in humans including smallpox, the common cold, chicken pox, influenza, shingles, herpes, polio, rabies. Ebola, hanta fever, and AIDS. Some types of cancer have been linked to viruses.

Pyrogens are agents which induce fever. Bacteria are a common source for the production of endotoxins which are pyrogenic agents. Furthermore, another detrimental effect of endotoxins is their known adjuvant effect which could potentially intensify immune responses against therapeutic drugs. The endotoxin limit set by the Food and Drug Administration (FDA) guidelines for most pharmaceutical products is for a single dose 0.5 ng endotoxin per kilogram body weight or 25 ng endotoxin/dose for a 50 kg adult. Due to their size and charge heterogeneity, separation of endotoxins from proteins in solution can often be difficult. Endotoxin inactivation by chemical methods are unsuitable because they are stable under extremes of temperature and pH which would destroy the proteins. Furthermore, due to their amphipathic nature, endotoxins tend to adhere to proteins in a fashion similar to detergents. In such cases, endotoxin activity often clusters with the protein when chromatographic procedures such as ion exchange chromatography or gel filtration are employed.

Presently, the purification of biomolecules is sometimes a long and cumbersome process especially when purifying blood proteins. The process is made all the more complex by the additional step of ensuring the product is "bug" free. The costs associated with this task is large and further escalates the purification costs in total. The Gradiflow technology rapidly purifies target proteins with high yield. For example, a proteins like fibrinogen (a clotting protein) can be separated in three hours using the Gradiflow while the present industrial separation is 3 days. Certain monoclonal antibodies can be purified in 35 minutes compared to present industrial methods which take 35 hours.

The membrane configuration in the Gradiflow enables the system to be configured so that the purification procedure can also include the separation of bacteria viruses and vectors. It has now been found by the present inventors that appropriate membranes can be used and the cartridge housing the membrane configured to include separate chambers for the isolated bacteria and viruses.

The Gradiflow Technology

Gradiflow is a unique preparative electrophoresis technology for macromolecule separation which utilises tangential flow across a polyacrylamide membrane when a charge is applied across the membrane (AU 601040). The general design of the Gradiflow system facilitates the purification of proteins and other macromolecules under near native conditions. This results in higher yields and excellent recovery.

In essence the Gradiflow technology is bundled into a cartridge comprising of three membranes housed in a system of specially engineered grids and gaskets which allow separation of macromolecules by charge and/or molecular weight. The system can also concentrate and desalt/dialyse at the same time. The multimodal nature of the system allows this technology to be used in a number of other areas especially in the production of biological components for medical use. The structure of the membranes may be configured so that bacteria and viruses can be separated at the point of separation—a task which is not currently available in the biotechnology industry and adds to the cost of production through time delays and also because of the complexity of the task.

DISCLOSURE OF INVENTION

In a first aspect, the present invention consists in a method of removing a biological contaminant from a mixture containing a biomolecule and the biological contaminant, the method comprising:

(a) placing the biomolecule and contaminant mixture in a first solvent stream, the first solvent stream being separated from a second solvent stream by an electrophoretic membrane;

(b) selecting a buffer for the first solvent stream having a required pH;

(c) applying an electric potential between the two solvent streams causing movement of the biomolecule through the membrane into the second solvent stream while the biological contaminant is substantially retained in the first sample stream, or if entering the membrane, being substantially prevented from entering the second solvent stream;

(d) optionally, periodically stopping and reversing the electric potential to cause movement of any biological contaminants having entered the membrane to move back into the first solvent stream, wherein substantially not causing any biomolecules that have entered the second solvent stream to re-enter first solvent stream; and (e) maintaining step (c), and optional step (d) if used, until the second solvent stream contains the desired purity of biomolecule.

In a second aspect, the present invention consists in a method of removing a biological contaminant from a mixture containing a biomolecule and the biological contaminant, the method comprising:

(a) placing the biomolecule and contaminant mixture in a first solvent stream, the first solvent stream being separated from a second solvent stream by an electrophoretic membrane;

(b) selecting a buffer for the first solvent stream having a required pH;

(c) applying an electric potential between the two solvent streams causing movement of the biological contaminant through the membrane into the second solvent stream while the biomolecule is substantially retained in the first sample stream, or if entering the membrane, being substantially prevented from entering the second solvent stream;

(d) optionally, periodically stopping and reversing the electric potential to cause movement of any biomolecule having entered the membrane to move back into the first solvent stream, wherein substantially not causing any biological contaminants that have entered the second solvent stream to reenter first solvent stream; and (e) maintaining step (c), and optional step (d) if used, until the first solvent stream contains the desired purity of biomolecule.

In the first and second aspects of the present invention, preferably the biomolecule is selected from the group consisting of blood protein, immunoglobulin, and recombinant protein.

The biological contaminant can be a virus, bacterium, prion or an unwanted biomolecule such as lipopolysaccharide, toxin or endotoxin.

Preferably, the biological contaminant is collected or removed from the first stream.

Preferably, the buffer for the first solvent stream has a pH lower than the isoelectric point of biomolecule to be separated.

In a further preferred embodiment of the first aspect of the present invention, the electrophoretic membrane has a molecular mass cut-off close to the apparent molecular mass of biomolecule. It will be appreciated, however, that the membrane may have any required molecular mass cut-off depending on the application. Usually, the electrophoretic membrane has a molecular mass cut-off of between about 3 and 1000 kDa. A number of different membranes may also be used in a desired or useful configuration.

The electric potential applied during the method is selected to ensure the required movement of the biomolecule, or contaminant if appropriate, through the membrane. An electric potential of up to about 300 volts has been found to be suitable. It will be appreciated, however, that greater or lower voltages may be used.

The benefits of the method according to the first aspect of the present invention are the possibility of scale-up, and the removal of biological contaminants present in the starting material without adversely altering the properties of the purified biomolecule.

In a third aspect, the present invention consists in use of Gradiflow in the purification or separation of biomolecule from a biological contaminant.

In a fourth aspect, the present invention consists in biomolecule substantially free from biological contaminants purified by the method according to the first aspect of the present invention.

In a fifth aspect, the present invention consists in use of biomolecule according to the third aspect of the present invention in medical and veterinary applications.

In a sixth aspect, the present invention consists in a substantially isolated biomolecule substantially free from biological contaminants.

Throughout this specification, unless the context requires otherwise, the word "comprise", or variations such as "comprises" or "comprising", will be understood to imply the inclusion of a stated element, integer or step, or group of elements, integers or steps, but not the exclusion of any other element, integer or step, or group of elements, integers or steps.

In order that the present invention may be more clearly understood a preferred forms will be described with reference to the accompanying drawings.

MODES FOR CARRYING OUT THE INVENTION

Figure 1:
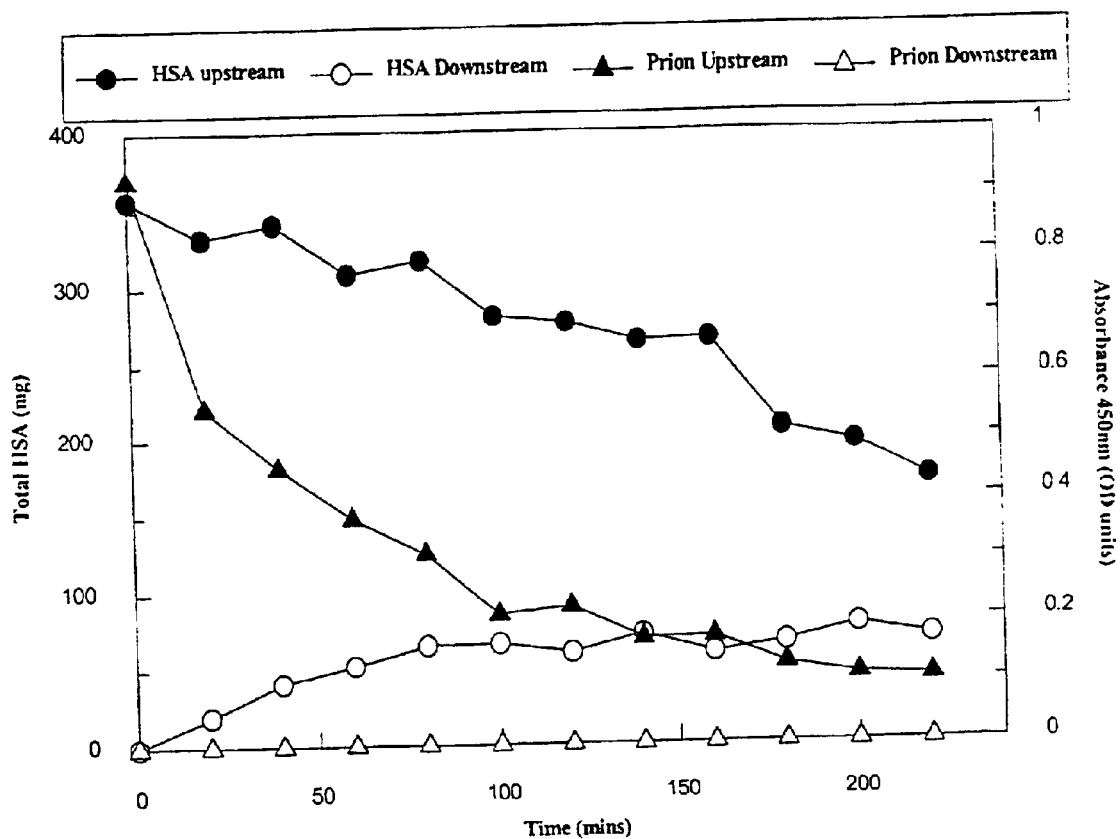
FIG. 1. Samples from up and downstream were taken at time intervals (x-axis) during the isolation of albumin from plasma. Albumin was measured in the samples by mixing with BCG reagent and reading the absorbance of 630 nm. The concentration of albumin in each sample was calculated from the standard curve, and multiplied by the volume of the up- or downstream to obtain the Total HSA in the up- and downstream (y-axis). All samples were assayed for prion using a sandwich ELISA, and recording the absorbance values at 450 nm (second y-axis).

Virus Removal During Plasma Protein Purification using Gradiflow Technology

Contamination with virus is a major concern when purifying plasma proteins, such as IgG and human serum albumin (HSA). A contaminant virus can potentially infect a patient receiving the contaminated plasma products. A virus that infects bacteria is known as a phage, and they are readily detected by examining culture plates for cleared zones in a coating or lawn of bacteria.

Aim. To isolate IgG, HSA, and Fibrinogen from human plasma spiked with virus, using the Gradiflow, with simultaneous removal of the contaminating virus.

IgG Purification Procedure

IgG is the most abundant of the immunoglobulins, representing almost 70% of the total immunoglobulins in human serum. This class of immunoglobulins has a molecular mass of approximately 150 kDa and consists of 4 subunits, two of which are light chains and two of which are heavy chains. The concentration of IgG in normal serum is approximately 10 mg/ml.

IgGs are conventionally purified using Protein A affinity columns in combination with DEAE-cellulose or DEAE-Sephadex columns. The main biological contaminants in IgG isolations are β-lipoprotein and transferrin. The product of conventional protein purification protocols is concentrated using ultrafiltration. Immunoaffinity can also be used to isolate specific IgGs.

Method: Platelet free plasma was diluted one part in three with Tris-borate, pH 9.0 running buffer and placed in the upstream of Gradiflow and spiked with either Llambda or T7 phage to a concentration of ~$10^8$ pfu/ml (plaque forming units/ml). A potential of 250V was placed across a separating membrane with a molecular weight cut off of 200 kDa (3 kDa restriction membranes). A membrane of this size restricts IgG migration whilst allowing smaller molecular weight contaminants to pass through the membrane, leaving IgG and other large molecular weight proteins in the upstream. A second purification phase was carried out using a GABA/Acetic acid buffer, pH 4.6 with a 500 kDa cut off separating membrane (3 kDa restriction membranes). A potential of 250V reversed polarity was placed across the system resulting in IgG migration through the membrane leaving other high molecular weight contaminants upstream.

Examination of samples taken at 30 minutes intervals was made on reduced SDS-PAGE 4–25% gels.

Virus Testing

One hundred and fifty μl taken at each time point sample was mixed with 100 μl of appropriate *Escherichia coli* culture (Strain HB101 was used for T7 and strain JM101 for Llambda). The mixtures were incubated for 15 minutes at 37° C. before each was added to 2.5 ml of freshly prepared molten soft agar, and vortexed. The mixtures were poured over culture plates of Luria Agar and incubated at 37° C. overnight. The plates were inspected for the presence of virus colonies (plaques) in the lawn of *E. coli*. The number of plaques was recorded or if the virus had infected the entire *E. coli* population the result was recorded as confluent lysis.

HSA Purification Procedure

Albumin is the most abundant protein component (50 mg/m.) in human plasma and functions to maintain blood volume and oncotic pressure. Albumin regulates the transport of protein, fatty acids, hormones and drugs in the body. Clinical uses include blood volume replacement during surgery, shock, serious burns and other medical emergencies. Albumin is 67 kDa and has an isoelectric point of approximately 4.9. The protein consists of a single subunit and is globular in shape. About 440 metric tons of albumin is used annually internationally with worldwide sales of US $1.5 billion. Albumin is currently purified using Cohn fractionation and commercial product contains many contaminants in addition to multimers of albumin. The high concentration, globular nature and solubility of albumin make it an ideal candidate for purification from plasma using Gradiflow technology.

Method: Pooled normal plasma was diluted one in three with Tris-Borate (TB) running buffer, pH 9.0 and spiked with ~10 pfu/ml of Llambda or T7 phage. The mixture was placed in the upstream of a Gradiflow apparatus. Albumin was isolated from platelet free plasma in a one-phase process using the charge of albumin at a pH above its isoelectric point (pI) and its molecular weight. Thus, a cartridge with a 75 kDa cutoff separation membrane was placed between two 50 kDa cutoff restriction membranes. The albumin was removed from high molecular weight contaminants by its migration through the separation membrane whilst small molecular weight contaminants dissipated through the 50 kDa restriction membrane. Samples were taken at regular intervals throughout a 90 minutes run.

The presence of the purified HSA in the downstream was demonstrated by examination by SDS-PAGE. Virus was detected as previously described above.

Fibrinogen Purification Procedure:

Commercially, fibrinogen has a role as fibrin glue, which is used to arrest bleeding and assist in the wound healing process. Fibrinogen is an elongated molecule of 340 kDa that consists of three non-identical subunit pairs that are linked by a disulphide knot in a coiled coil conformation. The isoelectric point of fibrinogen is 5.5 and it is sparingly soluble when compared with other plasma proteins.

Fibrinogen is conventionally purified from plasma by a series of techniques including ethanol precipitation, affinity columns and traditional electrophoresis. This process takes about 48–72 hours and the harsh physical and chemical stresses placed on fibrinogen are believed to denature the molecule, resulting in activity that is removed from that of fibrinogen in plasma.

Cryo-precipitation is the first step in the production of factor VIII and involves the loss of most of the fibrinogen in plasma. Processing of this waste fibrinogen is of considerable interest to major plasma processors and provides an opportunity to demonstrate the rapid purification of fibrinogen from cryo-precipitate using the Gradiflow.

Method. Cryo-precipitate 1, produced by thawing frozen plasma at 4° C. overnight was removed from plasma by centrifugation at 10000×g at 4° C. for 5 minutes. The precipitate was re-dissolved in Tris-Borate buffer (pH 9.0) and placed in the upstream of a Gradiflow apparatus. The upstream was spiked with either Llambda or T7 phage to a concentration of ~$10^8$ pfu/ml. A potential of 250V was applied across a 300 kDa cutoff cartridge and run for 2 hours. The downstream was replaced with fresh buffer at 30 minute intervals. A second phase was used to concentrate the fibrinogen through a 500 kDa cutoff separation membrane at pH 9.0. The downstream was harvested at 60 minutes. The product was dialysed against PBS pH 7.2 and analysed for clotting activity by the addition of calcium and thrombin (final concentrations 10 mM and 10NIH unit/ml respectively).

The presence of purified fibrinogen was confirmed by examination on reduced SDS PAGE 4–25% gels. The presence of either T7 or Llambda in the time point samples was tested using the previously described method.

Results of IgG, HSA and Fibrinogen Purification:

The procedures described successfully purified IgG, albumin and fibrinogen as judged by electrophoresis. Neither T7 nor Llambda phage were detected in the downstream products, but were present in the upstream samples.

Prion Removal During Plasma Protein Purification using Gradiflow Technology

There is an international concern regarding the contamination of plasma proteins by prion protein. Prion is a glycoprotein of 27–33 kDa in size which occurs naturally in many human derived materials, including white blood cells, platelets, plasma and plasma proteins preparations, e.g., HSA, IgG, FVIII and fibrinogen. Prion can become folded abnormally and cause neurological disorders such as Creutzfeld-Jacob disease (CJD) and Kuru. Currently, there is much concern regarding the transmission of these diseases via transfusion and plasma protein fractions administered clinically.

Aim: To isolate NSA from human plasma using the Gradiflow, with simultaneous removal of prion.

Method: Pooled platelet rich plasma was diluted one in two with Tris-Borate (TB) running buffer, pH 9.0 and was placed in the upstream of a Gradiflow apparatus. Albumin was isolated from platelet free plasma using the charge of albumin at a pH above its pI and its molecular weight. Thus, a cartridge with a 75 kDa cutoff separation membrane was placed between two 50 kDa cutoff restriction membranes. The albumin was removed from high molecular weight contaminants by its migration through the separation membrane whilst small molecular weight contaminants dissipated through the 50 kDa restriction membrane. Samples were taken at 20 minute intervals throughout a 240 minute run. The buffer stream and cartridge were replaced after the initial two hours, with identical solutions and cartridge.

The presence of the purified HSA in the downstream was demonstrated by examination by SDS-PAGE, and was measured using a Bromocresol Green Assay (purchase from Trace Scientific. Prion was tested for in both up- and down-stream samples using a sandwich ELISA comprised of prion specific antibodies obtained from Prionics Inc (Switzerland).

Albumin Quantitation

Fifty µl of each time point sample was diluted with 50 µl of PBS buffer. A 20 µl aliquot of each diluted sample was placed in a microplate well. A standard curve of the kit calibrator from a maximum concentration of 40 mg/ml was prepared using PBS as the diluent. The standard curve dilutions were also placed in the microplate (2 µl plasma/well). The bromocresol green reagent was added to all the wells (200 µl/well) and the absorbance at 630 nm was read using a Versamax microplate reader. The standard curve was drawn on a linear scale and the concentration of albumin in the up and downstream samples were read from the curve. The volume in the appropriate stream at the time of sampling was multiplied by the concentration of each sample. Thus providing a value for the total HSA present in each stream.

Prion Detection

A solution of 5 µg/ml monoclonal antibody denoted 6H4 (Prionics, Inc. Switzerland) in a 10 mM carbonate buffer was added to the wells of a microplate (100 µl/well), and incubated overnight at 4° C. The antibody was later decanted and the wells washed three times with 250 µl/well of a PBS solution containing 0.1% (v/v) Tween 20. The plate wells were blocked by incubating at room temperature for 30 minutes with 200 µl/well of PBS/T20 containing 1% albumin. The plate was again washed three times with 250 µl/well of PBS/T20 before the up and down-stream time point samples were added (100 µl/well). The samples were incubated for 1–2 hours at room temperature before being dispensed, and the plate washed three times as previously described. A solution of prion-specific polyclonal antibody, denoted R029 (Prionics Inc. Switzerland) was diluted at 1:1000 (v:v) in PBS/T20, and added to the wells of the plate (100 µl/well). The mixture was incubated for 1–2 hours at room temperature, before being decanted. The plate was washed three times and 100 µl/well of horseradish peroxidase conjugated polyclonal anti-rabbit IgG antiserum (purchased from Dakopatts) was added. The conjugate was incubated for 30–60 minutes at room temperature and then removed. Any bound HRP conjugate was detected using o-tolidine substrate solution (100 µl/well) and the reaction stopped by addition of 3M HCl (50 µl/well). The developed colour was measured at 450 nm in a Versamax plate reader.

Results

Albumin was transferred to the downstream and was detected in the BCG assay (FIG. 1), and visualized on a native 8–16% electrophoresis gel. Decreasing quantities of Prion were detected in the upstream during the time-course, and no Prion was detected in the downstream samples.

Endotoxin Removal During Plasma Protein Purification using Gradiflow Technology

Contamination with bacterial endotoxin is a major concern when purifying plasma proteins, such as IgG and HSA. Endotoxins are a lipopolysaccharide derived from the lipid membrane of gram negative bacteria. The presence of endotoxin in a human blood fraction therapeutic can lead to death of the receiving patients.

Aim: To isolate IgG and HSA from human plasma spiked with endotoxin, using the Gradiflow, with simultaneous removal of endotoxin.

IgG Purification Procedure

Method: Platelet free plasma was diluted one part in three with Tris-borate, pH 9.0 running buffer and placed in the upstream of a Gradiflow apparatus and spiked with purified $E.\ coli$ endotoxin to a concentration of 55 ng/ml. A potential of 250V was placed across a separating membrane with a molecular weight cut off of 200 kDa (3 kDa restriction membranes). A membrane of this size restricts IgG migration whilst allowing smaller molecular weight contaminants to pass through the membrane, leaving IgG and other large molecular weight proteins in the upstream. A second purification phase was carried out using a GABA/Acetic acid buffer, pH 4.6 with a 500 kDa cut off separating membrane (3 kDa restriction membranes). A potential of 250V reversed polarity was placed across the system resulting in IgG migration through the membrane leaving other high molecular weight contaminants upstream.

Examination of samples taken at 30 minutes intervals was made on reduced SDS-PAGE 4–25% gels. Endotoxin was tested for using a LAL Pyrochrome Chromogenic assay purchased from Cape Cod Associates. All samples were diluted 1 in 10 and the endotoxin assay was performed according to the manufacturer instructions.

HSA Purification Procedure

Method: Pooled normal plasma was diluted one in three with Tris-Borate (TB) running buffer, pH 9.0 and spiked with 55 ng/ml of purified endotoxin. The mixture was placed in the upstream of a Gradiflow apparatus. Albumin was isolated from platelet free plasma in a one-phase process using the charge of albumin at a pH above its pI and its molecular weight. Thus, a cartridge with a 75 kDa cutoff separation membrane was placed between two 50 kDa cutoff restriction membranes. The albumin was removed from high molecular weight contaminants by its migration through the separation membrane whilst small molecular weight contaminants dissipated through the 50 kDa restriction membrane. Samples were taken at regular intervals throughout a 90 minute run.

The presence of the purified HSA in the downstream was demonstrated by examination by SDS-PAGE. Endotoxin was tested for in both up- and down-stream samples using a LAL Chromogenic assay supplied by Cape Cod Associates. All samples were diluted 1 in 10 and the endotoxin assay was performed according to the manufacturer instructions.

Results of IgG and HSA Purification

Figure 2:
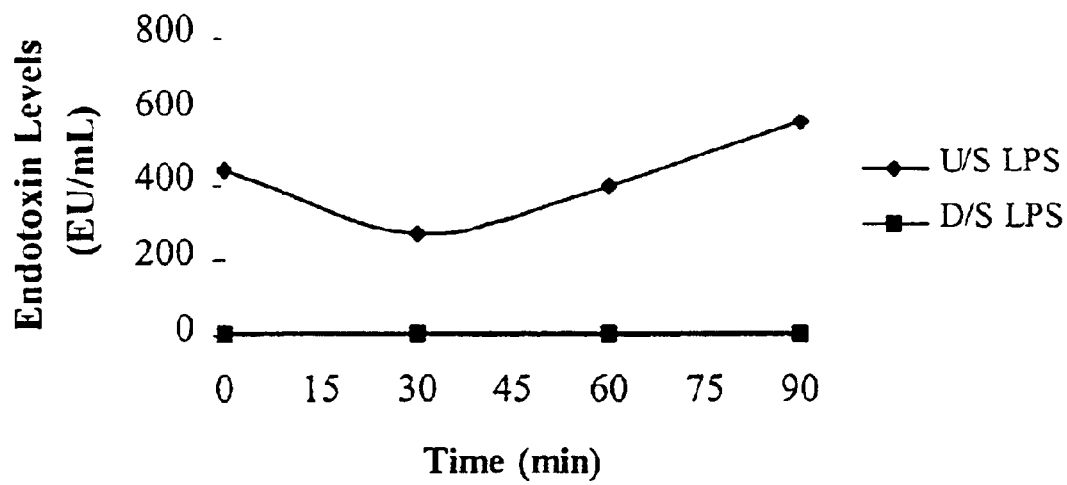
FIG. 2. Samples from the second phase of an IgG separation were taken from both up- and downstreams (U/S and D/S respectively) at 30 minute intervals. The samples were assayed for endotoxin using a LAL Chromogenic assay (Cape Cod Assoc.)

Up and downstream samples taken at 30 minute intervals during the second phase of an IgG purification from endotoxin spiked plasma were tested for endotoxin using a LAL Chromogenic assay. The results showed that the endotoxin was almost entirely found in the upstream at all time points (FIG. 2). The downstream contained only 0.7% of the initial endotoxin. Reduced SDS-PAGE examination showed that IgG had been successfully isolated in the downstream.

Analysis of samples taken at 30 minute intervals during the purification of HSA from plasma spiked with endotoxin found the majority of endotoxin remained in the upstream.

Figure 3:
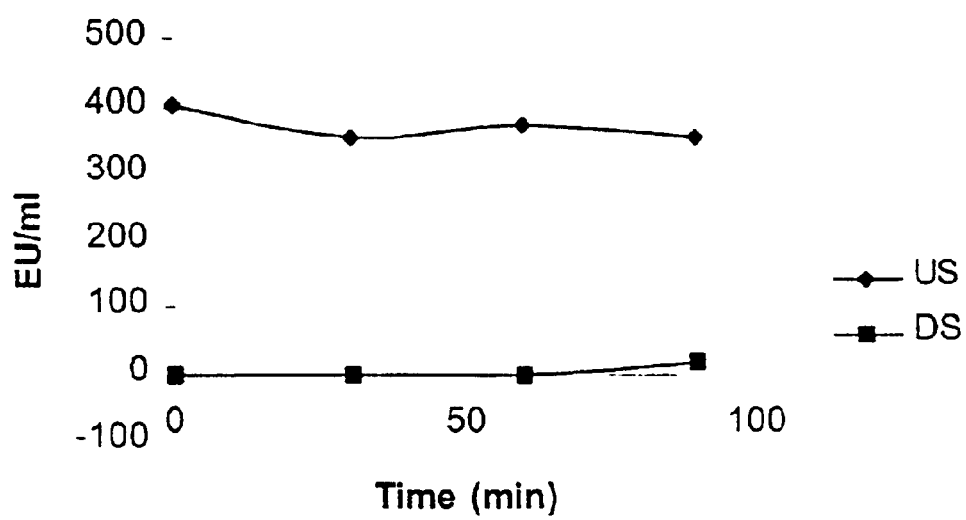
FIG. 3. HSA was purified from endotoxin spiked plasma. Samples were taken from up- and downstream at 30 minute intervals during a 90 minute purification (x-axis). Analysis of the samples using a LAL Chromogenic assay was performed to establish the endotoxin concentration (y-axis) in the samples.
Figure 4:
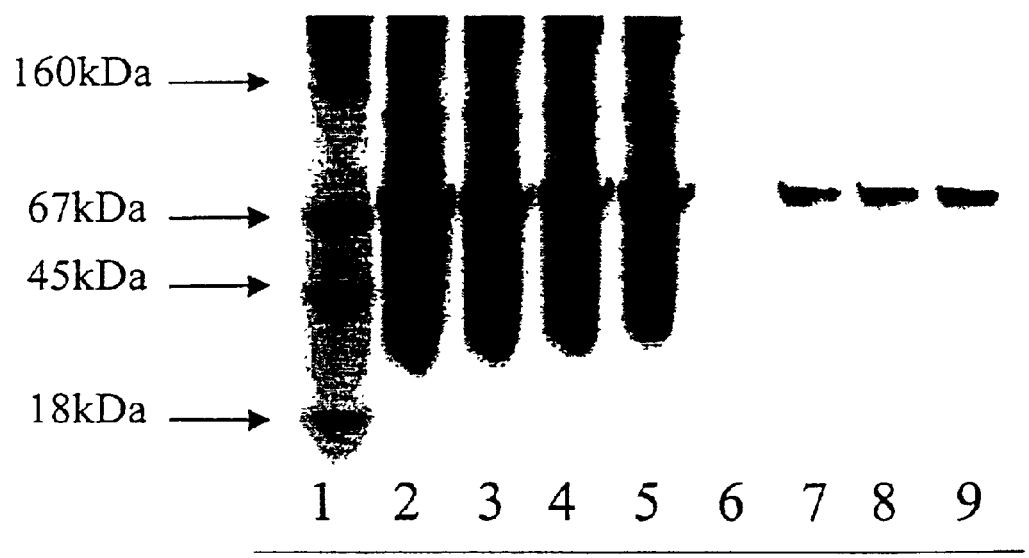
FIG. 4. Four to 25% native gel electrophoresis of samples from an HSA from endotoxin spiked plasma. Lane 1 contains molecular weight markers. Lane 2 contains starting plasma sample, Lanes 3–5 contain upstream samples at time 30, 60, and 90 minutes. Lanes 6–9 contain downstream samples at time 0, 30, 60 and 90 minutes, respectively.

Only 4% of the total endotoxin was found in the downstream at the end of the run (FIG. 3). Native PAGE examination confirmed the presence of purified HSA in the downstream samples (FIG. 4).

Bacteria Removal During Plasma Protein Purification using Gradiflow Technology

Contamination with bacteria is a major concern when purifying plasma proteins, such as IgG and HSA. Contaminant bacteria can potentially infect a patient receiving the plasma products, or during pasteurisation of the products the bacteria dies releasing dangerous endotoxins, that are harmful to the patient. Bacteria are easily detected by culturing samples on nutrient agar plates.

Aim: To isolate IgG and HSA, from human plasma spiked with bacteria, using the Gradiflow.

IgG Purification Procedure

Method: Platelet free plasma was diluted one part in three with Tris-borate, pH 9.0 running buffer and placed in the upstream of Gradiflow and spiked with *E. coil* to a concentration of $4 \times 10^8$ cells/ml. A potential of 250V was placed across a separating membrane with a molecular weight cut off of 200 kDa (100 kDa restriction membranes). A membrane of this size restricts IgG migration whilst allowing smaller molecular weight contaminants to pass through the membrane, leaving IgG and other large molecular weight proteins in the upstream. A second purification phase was carried out using a GABA/Acetic acid buffer, pH 4.6 with a 500 kDa cut off separating membrane (3 kDa restriction membranes). A potential of 250V reversed polarity was placed across the system resulting in IgG migration through the membrane leaving other high molecular weight contaminants upstream.

Examination of samples taken at 30 minutes intervals was made on reduced SDS-PAGE 4–25% gels.

Bacteria Testing

Twenty µl of upstream or 100 µl of downstream samples were spread plated onto Luria agar culture plates. The plates were incubated for 24 hours at 37° C., and the number of colonies was counted.

HSA Purification Procedure

Method: Pooled normal plasma was diluted one in three with Tris-Borate (TB) running buffer, pH 9.0 and spiked with $4 \times 10^8$ cells/ml of *E. coil*. The mixture was placed in the upstream of a Gradiflow apparatus. Albumin was isolated from platelet free plasma in a one-phase process using the charge of albumin at a pH above its pI and its molecular weight. Thus a cartridge with a 75 kDa cutoff separation membrane was placed between two 50 kDa cutoff restriction membranes. The albumin was removed from high molecular weight contaminants by its migration through the separation membrane whilst small molecular weight contaminants dissipated through the 50 kDa restriction membrane. Samples were taken at regular intervals throughout a 90 minutes run.

The presence of the purified HSA in the downstream was demonstrated by examination by SDS-PAGE. Bacteria were detected as previously described above.

Results of IgG and HSA Purification

The procedures described successfully purified IgG, and albumin as judged by electrophoretic examination. The downstream samples containing the purified protein products did not contain detectable *E. coli* colonies, while the upstream samples produced greatly in excess of 500 colonies/plate.

CONCLUSION

It is possible to purify proteins such as IgG, albumin and fibrinogen from plasma, while simultaneously removing contaminating virus by the methods according to the present invention.

Prion present in plasma can be moved across a 75 kDa separation membrane with albumin, however, unlike albumin, the prion is not retained by the 50 kDa restriction membrane. Thus, albumin can be purified from plasma with simultaneous removal of Prion protein.

Evidence has been provided by the present inventors that it is possible to purify proteins such as IgG and albumin from plasma, while simultaneously removing endotoxin contamination in the starting plasma using the Gradiflow technology.

Furthermore, it has been found that it is also possible to purify proteins such as IgG, and albumin from plasma, while simultaneously removing contaminating bacteria.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method of selectively removing a non-pathogenic biological contaminant from a mixture containing a compound and the contaminant comprising:
   (a) placing the compound and the contaminant mixture in a first solvent stream, the first solvent stream being separated from a second solvent stream by a selective membrane having a defined pore size;
   (b) selecting a buffer for the first solvent stream having a required pH;
   (c) applying an electric potential across the first and the second solvent streams, wherein at least a portion of the compound moves through the membrane into the second solvent stream while the contaminant is substantially retained in the first solvent stream, and substantially all transmembrane migration of the compound is initiated by application of the electric potential;
   (d) optionally, periodically stopping and reversing the electric potential whereby at least a substantial portion of the contaminant having entered the membrane moves back into the first solvent stream, while any of the compound that has entered the second solvent stream does not re-enter the first solvent stream; and
   (e) maintaining step (c), and optional step (d) if used, until the second solvent stream contains the desired purity of the compound.

2. The method according to claim 1 wherein the compound is selected from the group consisting of blood proteins, immunoglobulins, recombinant proteins, and combinations thereof.

3. The method according to claim 1 wherein the contaminant is selected from the group consisting of non-pathogenic bacteria, non-pathogenic viruses, lipopolysacchrides, toxins, endotoxins, and combinations thereof.

4. The method according to claim 3 wherein the contaminant is a lipopolysaccharide.

5. The method according to claim 3 wherein the contaminant is a toxin.

6. The method according to claim 3 wherein the contaminant is an endotoxin.

7. The method according to claim 3 wherein the solvent for the first solvent stream has a pH lower than the isoelectric point of the compound.

8. The method according to claim 3 wherein the selective membrane has a molecular mass cut-off of between about 3 kDa and about 80,000 kDa.

9. The method according to claim 3 wherein the electric potential is up to about 300 volts.

10. The method according to claim 3 wherein the selective membrane has a molecular cut-off close to the apparent molecular mass of the compound.

11. The method according to claim 3 wherein the solvent for the first solvent stream has a pH at about the isoelectric point of the compound.

12. The method according to claim 3 wherein the solvent for the first solvent stream has a pH above the isoelectric point of the compound.

13. The method according to claim 3 wherein the selective membrane has a molecular mass cut-off of at least about 3 kDa.

14. The method according to claim 3 wherein the compound is collected or removed from the second solvent stream.

15. The method according to claim 14 wherein the compound is substantially free of the contaminant.

16. The method according to claim 3 further comprising the step of applying the electric potential across a third solvent stream, wherein the third solvent stream is separated from the first or the second solvent stream by a second selective membrane, and at least one of the compound and the contaminant moves through the second membrane and into the third solvent stream.

17. The method according to claim 16 further comprising the step of applying the electric potential across a fourth solvent stream, wherein the fourth solvent stream is separated from the other of the first and the second solvent streams by a third selective membrane, and at least a portion of at least one of the compound and the contaminant moves through the third membrane and into the fourth solvent stream.

18. A method of selectively removing a non-pathogenic biological contaminant from a mixture containing a compound and the contaminant comprising:
(a) placing the compound and contaminant mixture in a first solvent stream, the first solvent stream being separated from a second solvent stream by a selective membrane having a defined pore size;
(b) selecting a buffer for the first solvent stream having a required pH;
(c) applying an electric potential across the first and the second solvent streams, wherein at least a portion of the contaminant moves through the membrane into the second solvent stream while the compound is substantially retained in the first solvent stream, and substantially all transmembrane migration of the contaminant is initiated by application of the electric potential;
(d) optionally, periodically stopping and reversing the electric potential whereby at least a substantial portion of the compound having entered the membrane move back into the first solvent stream, while any of the contaminant that has entered the second solvent stream does not re-enter the first solvent stream; and
(e) maintaining step (c), and optional step (d) if used, until the second solvent stream contains the desired purity of the compound.

19. The method according to claim 18 wherein the contaminant is selected from the group consisting of lipopolysaccharides, toxins, endotoxins, and combinations thereof.

20. The method according to claim 18 wherein the contaminant is a lipopolysaccharide.

21. The method according to claim 18 wherein the contaminant is a toxin.

22. The method according to claim 18 wherein the contaminant is an endotoxin.

23. The method according to claim 18 wherein the compound is selected from the group consisting of blood proteins, immunoglobulins, recombinant proteins, and combinations thereof.

24. The method according to claim 18 wherein the solvent for the first solvent stream has a pH lower than the isoelectric point of the contaminant.

25. The method according to claim 18 wherein the solvent for the first solvent stream has a pH at about the isoelectric point of the contaminant.

26. The method according to claim 18 wherein the solvent for the first solvent stream has a pH above the isoelectric point of the contaminant.

27. The method according to claim 18 wherein the selective membrane has a molecular mass cut-off close to the apparent molecular mass of the contaminant.

28. The method according to claim 18 wherein the selective membrane has a molecular mass cut-off of at least about 3 kDa.

29. The method according to claim 18 wherein the selective membrane has a molecular mass cut-off of between about 3 kDa and about 80,000 kDa.

30. The method according to claim 18 wherein the electric potential is up to about 300 volts.

31. The method according to claim 18 wherein the contaminant is collected or removed from the second solvent stream.

32. The method according to claim 18 wherein substantially all of the contaminant is removed from the mixture.

33. The method according to claim 18 wherein the mixture comprises at least two types of contaminant and only one type moves into the second solvent stream.

34. The method according to claim 18 further comprising the step of applying the electric potential across a third solvent stream, wherein the third solvent stream is separated from the first or the second solvent stream by a second selective membrane, and at least a portion of at least one of the compound and the contaminant moves through the second selective membrane and into the third solvent stream.

35. The method according to claim 34 further comprising the step of applying the electric potential across a fourth solvent stream, wherein the fourth solvent stream is separated from the other of the first and the second solvent streams by a third selective membrane, and at least a portion of at least one of the compound and the the contaminant moves through the third selective membrane and into the fourth solvent stream.

* * * * *